United States Patent [19]

Lin et al.

[11] 4,427,525

[45] * Jan. 24, 1984

[54] DUAL GAS MEASURING SOLID ELECTROLYTE ELECTROCHEMICAL CELL APPARATUS

[75] Inventors: Ching Y. Lin, Monroeville; Chikara Hirayama, Franklin, both of Pa.

[73] Assignee: Westinghouse Electric Corp., Pittsburgh, Pa.

[*] Notice: The portion of the term of this patent subsequent to Mar. 22, 2000 has been disclaimed.

[21] Appl. No.: 381,091

[22] Filed: May 24, 1982

[51] Int. Cl.$^3$ ............................................. G01N 27/46
[52] U.S. Cl. .................................. 204/427; 204/412; 204/424; 204/428
[58] Field of Search ............... 204/424, 426, 427, 428, 204/429

[56] References Cited

U.S. PATENT DOCUMENTS 4,158,166 6/1979 Isenberg .............................. 204/426
4,377,460 3/1982 Lin et al. ............................. 204/426

FOREIGN PATENT DOCUMENTS 1040264 10/1978 Canada ................................ 204/426

Primary Examiner—R. L. Andrews
Assistant Examiner—Terryence F. Chipman
Attorney, Agent, or Firm—T. R. Trempus

[57] ABSTRACT

A dual gas measuring solid electrolyte apparatus employing a common oxygen ion conductive solid electrolyte membrane provides an electrical signal indicative of a selected anhydride of a monitored gas environment and an electrical signal indicative of the oxygen content of the monitored gas environment.

5 Claims, 2 Drawing Figures

DUAL GAS MEASURING SOLID ELECTROLYTE ELECTROCHEMICAL CELL APPARATUS

BACKGROUND OF THE INVENTION

The requirements for monitoring and controlling stack gas pollutants have resulted in the development of solid electrolyte gas sensors having electrolyte compositions uniquely responsive to gaseous pollutants such as $SO_x$, $CO_x$ and $NO_x$. Solid electrolyte sensors for monitoring gases containing anhydrides or related compounds in air or in oxygen-bearing gases have been described in detail in Canadian Pat. Nos. 1,002,599 and 1,040,264, both of which have been assigned to the assignee of the present invention and are incorporated herein by reference. In typical industrial installations a separate solid electrolyte gas sensor is employed to measure oxygen in the stack gas environment. The above-referenced sensors are electrochemical concentration cells which sense the equilibrium of a gas species of interest and generate a Nernst equation EMF signal corresponding to the difference in partial pressure of the gas species across the solid electrolyte sensor. Typically, the solid state sensor includes an ion conductive solid electrolyte with electrodes disposed on opposite surfaces thereof. The stack gas, or monitored gas environment, contacts a sensing electrode while the opposite electrode serves as a reference electrode. Conventional solid electrolyte compositions require operating temperatures of between about 600° C. and 900° C. to exhibit the desired ion conductivity to generate a suitable EMF signal. The accuracy of the EMF measurement depends in part on the effective sealing, or isolation, of the reference electrode from the monitored gas environment contacting the sensing electrode of the electrochemical cell. This isolation, or sealing requirement, at elevated operating temperatures has resulted in numerous expensive and complicated designs to achieve the desired isolation.

SUMMARY OF THE INVENTION

There is described herein with reference to the accompanying drawings a simple and effective technique for providing the desired isolation between the monitored gas environment and the reference gas environment of a solid electrolyte electrochemical cell assembly while utilizing a dual solid electrolyte cell configuration assembly consisting of a first and second cell configuration to provide signals indicative of both oxygen and a selected anhydride, i.e., $SO_2$, $CO_2$, etc. The first solid electrolyte cell configuration consists of two identical half cells, each consisting of a disc electrolyte element exhibiting ion conductivity of the selected anhydride at elevated temperatures and having an electrode disposed in intimate contact with one surface thereof. The opposite surfaces of the solid electrolyte disc elements are secured in contact with the opposite surfaces of the closed end of a closed-end solid tubular membrane of a material composition exhibiting oxygen anion conductivity at elevated temperatures and including an impurity content (i.e. Na, K, etc.) sufficient to support the alkali cation conductivity of interest. Suitable membrane compositions include stabilized zirconia and thoria. Electrodes are disposed on opposite surfaces of the tubular portion of the membrane to form an oxygen responsive solid electrolyte sensor as the second cell configuration.

The combination of the cell configurations on the tubular membrane are positioned with a housing to expose the reference electrodes of said cell configurations to a reference gas environment and the sensing electrodes to a monitored gas environment. The closed-end tubular ceramic membrane effectively isolates the reference gas environment from the monitored gas environment.

An anhydride measuring solid electrolyte apparatus employing identical half cells disposed on either side of the closed end of a tubular electrolyte exhibiting anhydride ion conductivity is described in pending U.S. patent application Ser. No. 312,552, entitled "Improved Solid Electrolyte Gas Sensing Apparatus", filed Oct. 19, 1981 and assigned to the assignee of the present invention.

BRIEF DESCRIPTION OF THE DRAWINGS

The invention will become more readily apparent from the following exemplary description in connection with the accompanying drawings.

DESCRIPTION OF THE PREFERRED EMBODIMENT

Suitable alkali cation conductive solid electrolyte compositions can be selected to render a solid electrolyte electrochemical cell suitable for measuring $SO_x$, $CO_x$, $NO_x$, etc. Commercially available oxygen-measuring cells typically employ oxygen anion conductive, calcia stabilized, zirconia ($ZrO_2 \cdot CaO$) as the electrolyte material. A detailed description of oxygen anion conductive material compositions and concentration cell configurations suitable for oxygen measurements using solid electrolyte electrochemical cells is provided in U.S. Pat. No. Re. 28,792 which is assigned to the assignee of the present invention and is incorporated herein by reference. Suitable electrolyte compositions for supporting alkali cation conductivity for the measurement of $SO_2$ in the monitored gas environment include $K_2SO_4$ and $Na_2SO_4$. Electrolyte compositions comprising $Na_2CO_3$ and $NaNO_3$ provide electrochemical cell ion conductivity to produce an EMF signal indicative of the $CO_2$ and $NO_2$ content respectively of a monitored gas environment.

Figure 1:
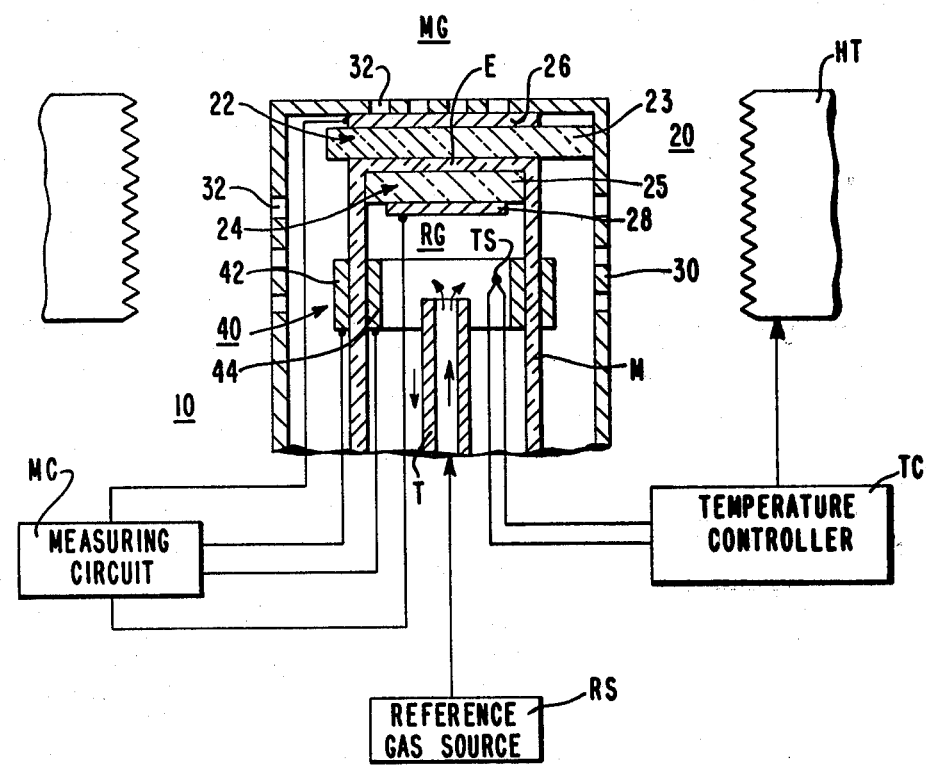
FIG. 1 is an enlarged sectioned illustration of a gas probe assembly incorporating a solid electrolyte electrochemical cell assembly in accordance with the disclosed inventive technique; and, FIG. 2 is a sectioned illustration of a novel assembly of FIG. 1 within a gas probe housing.

Referring to FIG. 1 there is illustrated a multi-constituent gas measuring probe apparatus 10 including a first solid electrolyte cell assembly 20 and a second solid electrolyte cell assembly 40. The solid electrolyte electrochemical concentration cell assembly 20 consists of identical alkali cation conductive half cells 22 and 24 comprised of solid electrolyte element 23 and sensing electrode 26, and solid electrolyte element 25 and reference electrode 28 respectively. The half cells 22 and 24 are secured to opposite surfaces of the closed end E of a closed-end ceramic tubular membrane M. The sensing electrode 26 of the electrochemical cell assembly 20 is disposed in contact with a surface of the electrolyte element 23 opposite from the surface contacting the membrane M, while the reference electrode 28 is in intimate contact with the surface of the electrolyte element 25 opposite the electrolyte element surface contacting the membrane M.

Most ceramic materials contain alkali ion impurities, i.e., Na, K, etc. It has been determined experimentally that this impurity content in conventional oxygen ion conductive solid electrolytes, such as stabilized zirconia, enables a membrane M comprised of such a composition to support cell assemblies for measuring both the anhydride and the oxygen content of a monitored gas environment. The implementation of an oxygen measuring cell assembly 40 is achieved by disposing a sensing electrode 42 and a reference electrode 44 on opposite surfaces of the tubular portion of the membrane M.

An impurity content in a range from about 0.01% to about 0.1% will enable the membrane M to support the alkali cation conductivity of the cell assembly 20.

The electrochemical cell assemblies 20 and 40 located within the tubular housing 30 having apertures 32 therein to permit the monitored gas environment MG to enter the housing 30 and contact the sensing electrodes 26 and 42. A reference gas RG, having a stable or known concentration of oxygen and the anhydride of interest, i.e. $SO_2$, is supplied by an inlet tube T from a remote reference gas source RS for contact with the reference electrodes 28 and 44. The EMF signals developed by the cell assemblies in response to changes in the oxygen and an anhydride content of the monitored gas environment are supplied to the measuring circuit MC. A temperature controller TC responds to the electrochemical cell operating temperature as measured by the temperature sensor TS to control the heater H to maintain the operating temperature of the cell assemblies 20 and 40 essentially constant.

The closed-end tubular membrane M provides the required isolation between the monitored gas environment MG and the reference gas environment RG while supporting both oxygen anion and alkali cation conduction. This dual conduction capability enables the cell assemblies 20 and 40 to generate EMF electrical signals indicative of the selected anhydride content and the oxygen content respectively of the monitored gas environment MG.

Assuming a $K_2SO_4$ composition for solid electrolyte elements 23 and 25, the cell assembly 20 may best be described by the cell notation:

$$\begin{pmatrix} \text{Reference} \\ \text{Environment} \end{pmatrix} \qquad \begin{pmatrix} \text{Monitored Gas} \\ \text{Environment} \end{pmatrix}$$
$$(SO_2 + O_2), Pt|K_2SO_4|ZrO_2|K_2SO_4|Pt, (SO_2 + O_2)$$

The EMF of the cell assembly 20 corresponds to that of the cell assembly $[(SO_2+O_2), Pt|K_2SO_4|Pt, (SO_2+O_2)]$ of the above-referenced Canadian patents and is represented as:

$$E = \frac{RT}{2F} \ln \frac{P_{SO_2} \cdot P_{O_2}}{P'_{SO_2} \cdot P'_{O_2}} \qquad (1)$$

In this embodiment of cell assembly 20, the current is carried by the $K^+$ ions in the $K_2SO_4$ while the $O^=$ ion is the current carrier in the $ZrO_2$ membrane M. However, the membrane M must be electrically neutral at all times. Therefore, if $O^=$ ion goes from the right to left in the above notation, the $O^=$ must be replaced by more $O^=$ ions at the right hand $ZrO_2|K_2SO_4$ interface. If oxygen ion conduction is the mechanism by which the cell assembly 20 operates, equation (1) would not apply for the coefficient on the right hand side of the notation. It would be RT/4 F rather than RT/2F. It has been determined experimentally however that the operation of the cell assembly 20 obeys equation (1). Therefore, the mechanism of the cell operation is that in which $K^+$ ion conduction controls the voltage of cell assembly 20. When the cell assembly voltage is measured with a measuring circuit MC which has a high impedance, so as not to draw current through the cell assembly 20, cell equilibration is rapidly attained due to the high conductivity of the $ZrO_2$ membrane M. As the $O^=$ ion drifts toward the $K_2SO_4|ZrO_2$ interface, the $K^+$ impurity ion drifts to the right, so that the net effect is similar to not having the membrane M as far as the cell voltage is concerned. Therefore, the EMF of the cell assembly 20 is a measure of the selected anhydride of the monitored gas environment MG in accordance with equation (1).

The EMF signal of the cell assembly 40 is a measurement of the oxygen content of the monitored gas environment MG as represented:

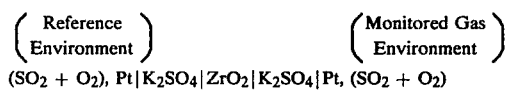

$$E = \frac{RT}{4F} \ln \frac{P_{O_2} \text{ (monitored environment)}}{P'_{O_2} \text{ (reference environment)}} \qquad (2)$$

The structure of apparatus 10 uniquely combines the dual cell operations of equations (1) and (2) into a single system. Since variations in the oxygen content of the monitored gas environment MG affect the EMF measurement of equation (1), the measuring circuit MC uses the EMF signal developed by the oxygen measuring cell assembly 40 to compensate for the oxygen variable in the EMF from the cell assembly 40 and produce a manifestation of the anhydride content of the monitored gas environment MG.

Figure 2:
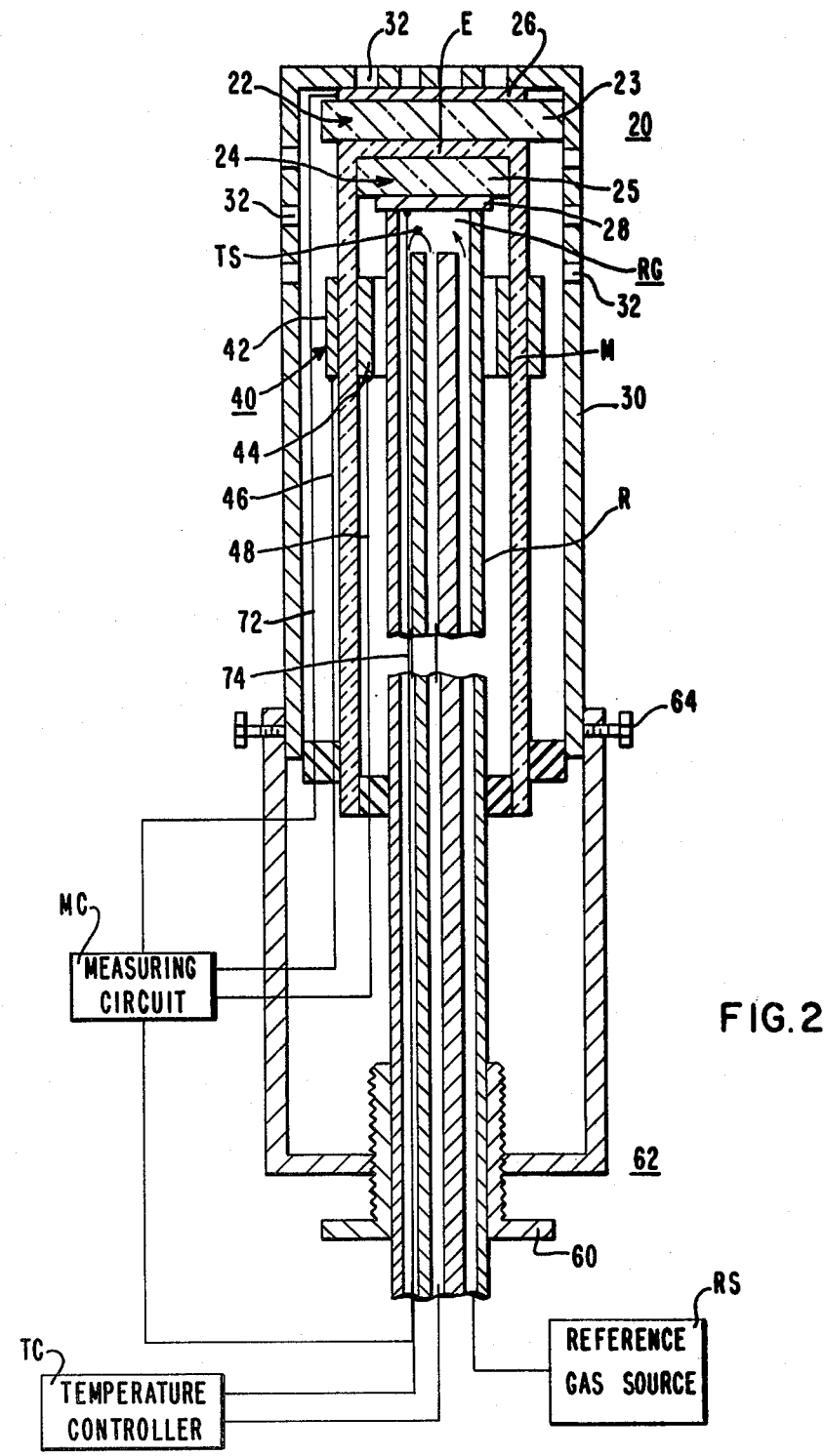

A preferred mechanical assembly of the gas probe apparatus 10 is illustrated in FIG. 2. The solid electrolyte element 23 of half cell 22 is first cemented onto the external surface of the closed end E of the oxygen anion conductive tubular membrane M. A platinum screen is formed around the surface of the solid electrolyte element 23 to form a porous, resilient sensing electrode 26. The tubular ceramic membrane M is then inserted within the protective housing 30 with the electrode 26 contacting the apertured end 32 of the housing of the tubular housing 30. A small quantity of solid electrolyte powder, i.e., $K_2SO_4$, is positioned on the internal surface of the closed end E of the alkali ion conductive solid membrane M to assure the desired contact with the solid electrolyte element 25 of half cell 24 which is mechanically inserted into the membrane M and in contact with the closed end thereof. Platinum screen material secured to the end of a tubular rod member R serves as a porous, resilient reference electrode 28. The tubular rod member R, which may be typically constructed of alumina, includes passages to accommodate the temperature sensor TS, electrode leads 72 and 74, and the flow of the reference gas from a remote reference gas source through the porous platinum screen electrode comprising reference electrode 28 to produce the reference gas environment RG. In the event the solid electrolyte elements 23 and 25 consist of $K_2SO_4$ compositions, the reference gas environment RG would be an $SO_2$ gas environment. The combination of the tubular rod member R and the electrode 28 secured to the open end thereof is separately inserted within the tubular membrane M. The opposite end of the rod member R is attached to a threaded manual screw adjustment 60 of a mechanical mounting fixture 62 which is secured to the outside surface of the tubular housing 30 by set screws 64. The fixture 60 aligns the rod member R within the tubular ceramic membrane M and the rotation of the screw adjustment 60 applies mechanical pressure against the combination of the half cell 24, the closed end E of the tubular membrane M, and the half cell 22 to mechanically secure the combination in contact with the apertured end 32 of the tubular housing 30. This arrangement permits easy removal and replacement of the membrane M and the half cells 22 and 24. Electrical leads 72 and 74 extend from electrodes 26 and 28 respectively to the EMF measuring circuit MC.

Electrical leads 46 and 48 extend from the electrodes 42 and 44 respectively of the oxygen measuring solid electrolyte cell assembly 40 to the measuring circuit MC.

We claim:

1. A gas analyzer apparatus for measuring gases of a monitored gas environment which contain anhydrides or related compounds in air or in oxygen-bearing gases by generating electrical signals on the basis of a difference in the partial pressure of a gas species between the monitored gas environment and a reference environment, comprising:

an anhydride monitoring solid electrolyte electrochemical cell assembly including first and second identical half cells, said first half cell including an alkali cation conductive solid electrolyte element and a sensing electrode disposed on a surface thereof, and said second half cell including an alkali cation conductive solid electrolyte element and a reference electrode disposed on a surface thereof, a solid membrane means of a composition exhibiting oxygen anion conductivity and including an impurity content to support alkali cation conductivity corresponding to the alkali cation conductivity of said half cells, the surface of said first half cell opposite the sensing electrode being in contact with a surface of said solid membrane means at a first location of said solid membrane means, the surface of said second half cell opposite the reference electrode being in contact with an opposite surface of said solid membrane means at said first location;

a sensing and a reference electrode disposed on opposite surfaces of said solid membrane means at a second location of said solid membrane means, the combination of said electrodes and said solid membrane means at said second location forming an oxygen monitoring solid electrolyte electrochemical cell, said monitored gas environment contacting the sensing electrodes of said first cell and said oxygen monitoring solid electrolyte electrochemical cell;

an anhydride reference means for maintaining an anhydride reference environment in contact with the reference electrode of said second half cell;

an oxygen reference means for maintaining an oxygen reference environment in contact with the reference electrode of said oxygen monitoring solid electrolyte electrochemical cell;

said solid membrane means isolating said monitored gas environment from said reference gas environments said anhydride monitoring solid electrolyte electrochemical cell assembly developing an electrical signal indicative of both the anhydride content and oxygen content of the monitored gas environment, said oxygen monitoring solid electrolyte electrochemical cell developing an electrical signal indicative of the oxygen content of the monitored gas environment.

2. Apparatus as claimed in claim 1 wherein the impurity content of the solid membrane means is in a range of about 0.01% to about 0.1%.

3. Apparatus as claimed in claim 1 wherein the material composition of said solid membrane means is selected from a group consisting of stabilized zirconia and stabilized thoria.

4. Apparatus as claimed in claim 1 further including circuit means connected to said anhydride monitoring cell assembly and said oxygen monitoring cell to subtract the electrical signal of said oxygen monitoring cell from the electrical signal of said anhydride monitoring cell assembly to produce a signal indicative of the anhydride content of the monitored gas environment.

5. Apparatus as claimed in claim 1 wherein said solid membrane means is a closed end tubular member, said first and second half cells being disposed in contact with either side of said closed end, said closed end being said first location of said solid membrane means, said second location of said membrane means being at a tubular portion of said solid membrane means.

* * * * *